United States Patent [19]

Kamhi

[11] Patent Number: 5,359,089

[45] Date of Patent: Oct. 25, 1994

[54] PROCESS FOR THE PREPARATION OF 2,4,5-TRIBROMOPYRROLE-3-CARBONITRILE

[75] Inventor: Victor M. Kamhi, Hamilton Square, N.J.

[73] Assignee: American Cyanamid Company, Wayne, N.J.

[21] Appl. No.: 172,452

[22] Filed: Dec. 22, 1993

[51] Int. Cl.$^5$ .................................. C07D 207/34
[52] U.S. Cl. .................................... 548/561
[58] Field of Search ........................... 548/561

[56] References Cited

U.S. PATENT DOCUMENTS 5,008,403  4/1991  Kameswaran ................. 548/561
5,204,332  4/1993  Brown et al. ................... 548/561

OTHER PUBLICATIONS

J. T. Gupton, et al, Journal of Organic Chemistry, 55, pp. 4735–4740 (1990).
A. M. van Leusen, et al, Tetrahedron Letters, pp. 5337–5340 (1972).
C. Reichardt and W. Kermer, Synthesis, 1970, p. 538.
J. Kucera and Z. Arnold, Collection Czechoslov. Chem. Commun., 32, pp. 1704–1711 (1967).
CA 115:71388m Decylative ... compounds. Kameswaran, p. 773, 1991.
CA 117:131061c Process for ... dihalomethanes. Kameswaren, p. 730, 1992.
CA 117:212309s Preparation of ... agents. Kameswaran, p. 823, 1992.

Primary Examiner—Johann Richter
Assistant Examiner—Joseph K. McKane
Attorney, Agent, or Firm—Michael P. Morris

[57] ABSTRACT

There is provided a process for the preparation of 2,4,5-tribromopyrrole-3-carbonitrile. 2,4,5-Tribromo-pyrrole-3-carbonitrile is useful as a molluscicidal agent.

11 Claims, No Drawings

PROCESS FOR THE PREPARATION OF 2,4,5-TRIBROMOPYRROLE-3-CARBONITRILE

BACKGROUND OF THE INVENTION

Pyrrole carbonitrile and nitropyrrole compounds are disclosed to be useful as insecticidal, acaricidal and molluscicidal agents in U.S. Pat. Nos. 5,162,308 and 5,204,332. Those patents also refer to 2,4,5-tribromopyrrole-3-carbonitrile, its molluscicidal use and its preparation via bromination of pyrrole-3-carbonitrile. However, pyrrole-3-carbonitrile and its derivatives are difficult to prepare. Literature methods, such as that reported by A. M. van Leusen, et al., Tetrahedron Letters, 5337, (1972), report yields of 10% or less.

The preparation of 2,4,5-tribromopyrrole-3-carbonitrile from 2-trihaloacetylpyrrole-4-carbonitrile compounds is described in United States Patent 5,008,403. However, that process is not well suited for use in large scale preparations of 2,4,5-tribromopyrrole-3-carbonitrile.

It is therefore an object of the present invention to provide a new and efficient process for preparing 2,4,5-tribromopyrrole-3-carbonitrile.

SUMMARY OF THE INVENTION

The present invention relates to a process for the preparation of molluscicidal 2,4,5-tribromopyrrole-3-carbonitrile.

Surprisingly, it has been found that 2,4,5-tribromopyrrole-3-carbonitrile is prepared by reacting a vinamidinium salt of formula I

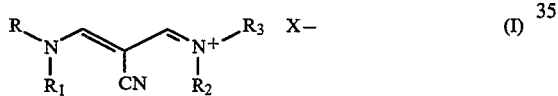

wherein
R, $R_1$, $R_2$ and $R_3$ are each independently $C_1$–$C_4$ alkyl, or when taken together, R and $R_1$, and $R_2$ and $R_3$, may form a 5- or 6-membered ring in which each of $RR_1$ and $R_2R_3$ are represented by the structure —$(CH_2)_4$— or —$(CH_2)_5$—; and
$X^-$ is an anion;
with a glycine ester of formula II

wherein $R_4$ is $C_1$–$C_4$ alkyl;
and a first base in the presence of a first solvent to form a mixture comprising 4-cyanopyrrole-2-carboxylic acid and a 4-cyanopyrrole-2-carboxylate of formula III

wherein $R_4$ is as described above, hydrolyzing said mixture with a second base in the presence of a second solvent to form a 4-cyanopyrrole-2-carboxylic acid salt, and reacting said 4-cyanopyrrole-2-carboxylic acid salt with a third base and a brominating agent in the presence of a third solvent to form the desired 2,4,5-tribromo-pyrrole-3-carbonitrile compound.

DETAILED DESCRIPTION OF THE INVENTION

Advantageously, the present invention provides a process for the preparation of 2,4,5-tribromopyrrole-3-carbonitrile which avoids the use and handling of toxic reagents such as chlorosulfonyl isocyanate.

Surprisingly, it has been found that 2,4,5-tribromopyrrole-3-carbonitrile is prepared by reacting a vinamidinium salt of formula I

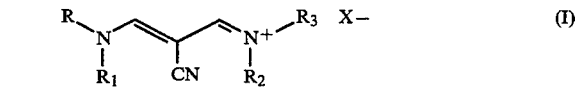

wherein
R, $R_1$, $R_2$ and $R_3$ are each independently $C_1$–$C_4$ alkyl, or when taken together, R and $R_1$, and $R_2$ and $R_3$, may form a 5- or 6-membered ring in which each of $RR_1$ and $R_2R_3$ are represented by the structure —$(CH_2)_4$— or —$(CH_2)5$—; and
$X^-$ is an anion;
with a glycine ester of formula II

wherein $R_4$ is $C_1$–$C_4$ alkyl;
and a first base in the presence of a first solvent to form a mixture comprising 4-cyanopyrrole-2-carboxylic acid and a 4-cyanopyrrole-2-carboxylate of formula III

wherein $R_4$ is as described above, hydrolyzing said mixture with a second base in the presence of a second solvent to form a 4-cyanopyrrole-2-carboxylic acid salt, and reacting said 4-cyanopyrrole-2-carboxylic acid salt with a third base and a brominating agent in the presence of a third solvent to form the desired 2,4,5-tribromo-pyrrole-3-carbonitrile compound.

A preferred process of the present invention comprises reacting a formula I vinamidinium salt with about 1 to 5 molar equivalents of a formula II glycine ester and about 2 to 6 molar equivalents of a first base in the presence of a first solvent at a temperature range of about 50° C. to 140° C. to form a mixture comprising 4-cyanopyrrole-2-carboxylic acid and a formula III 4-cyanopyrrole-2-carboxylate, hydrolyzing said mixture with about 1 to 8 molar equivalents of a second base in the presence of a second solvent at a temperature range of about 25° C. to 90° C. to form a 4-cyanopyrrole-2-carboxylic acid salt, and reacting said 4-cyanopyrrole-2-carboxylic acid salt with about 4 to 8 molar equivalents of a third base and about 3 to 9 molar equivalents of a brominating agent in the presence of a third solvent at a temperature range of about 0° C. to 25° C. to form the desired 2,4,5-tribromopyrrole-3-carbonitrile compound. The reaction scheme is illustrated in Flow Diagram I.

FLOW DIAGRAM I

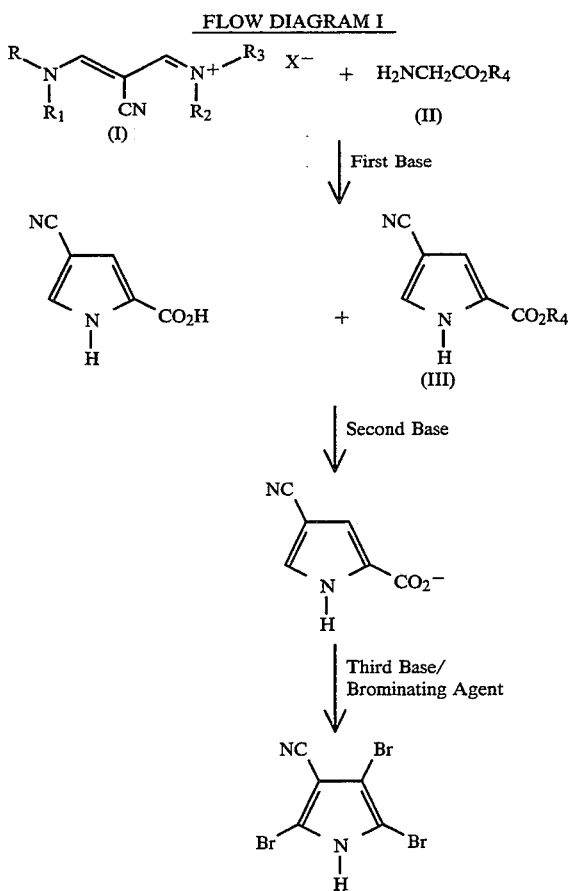

The product, 2,4,5-tribromopyrrole-3-carbonitrile, may be isolated by dilution of the reaction mixture with water, acidification of the diluted reaction mixture, and filtration of the product or extraction of the product with a suitable solvent. Suitable extraction solvents include substantially water-immiscible solvents such as ether, ethyl acetate, toluene, methylene chloride and the like.

First bases suitable for use in the process of the present invention are bases such as alkali metal $C_1$-$C_6$alkoxides and alkaline earth metal $C_1$-$C_6$alkoxides, with sodium methoxide being preferred. Second and third bases suitable for use in the process of the present invention are bases such as alkali metal hydroxides and alkaline earth metal hydroxides, with sodium hydroxide being preferred.

Brominating agents suitable for use in the process of the present invention include bromine, pyridinium bromide perbromide and N-bromosuccinimide, with bromine being preferred.

First solvents such as N,N-dimethylformamide, $C_1$-$C_4$alcohols, N,N-dimethylacetamide, dimethyl sulfoxide and N-methylpyrrolidone may be employed in the process of the present invention. Preferred first solvents include N,N-dimethylformamide and $C_1$-$C_4$alcohols, with N,N-dimethylformamide being most preferred. Second and third solvents suitable for use in the process of the present invention include water-miscible ethers such as tetrahydrofuran, dioxane, 2-methoxyethyl ether and 1,2-dimethoxyethane, water, and mixtures thereof. Preferred second and third solvents include dioxane, tetrahydrofuran, water, and mixtures thereof.

Preferred formula I vinamidinium salts which are suitable for use in the process of the present invention are those wherein R, $R_1$, $R_2$ and $R_3$ are each independently $C_1$-$C_4$alkyl; and $X^-$ is selected from the group consisting of $BF_4^-$, $ClO_4^-$, $HO_2CCO_2^-$ and $Cl^-$.

Most preferred formula I vinamidinium salts are those wherein

R, $R_1$, $R_2$ and $R_3$ are methyl; and $X^-$ is $HO_2CCO_2^-$.

Formula I vinamidinium salts may be prepared according to the procedures of C. Reichardt and W. Kermer, Synthesis, 1970, page 538; and J. Kucera and Z. Arnold, Collection Czechoslov. Chem. Commun., 32, pp. 1704–1711 (1967). Formula I vinamidinium chloride salts may be converted into the corresponding perchlorate, tetrafluoroborate or oxalate salts by conventional, well-known methods.

In order to facilitate a further understanding of the invention, the following examples are presented to illustrate more specific details thereof. The invention is not to be limited thereby except as defined in the claims.

EXAMPLE 1

Preparation of [2-Cyano- 3-(dimethylamino) -allylidene] dimethylammonium oxalate

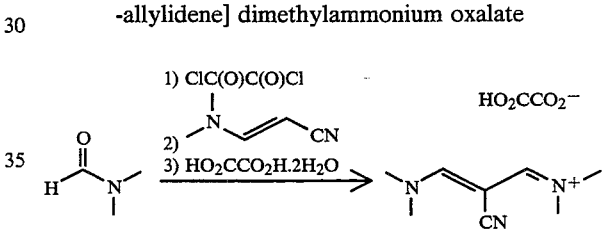

A solution of oxalyl chloride (13.1 mL, 0.15 mol) in 1,2-dichloroethane is added dropwise to a solution of N,N-dimethylformamide (11.6 mL, 0.15 mol) in 1,2-dichloroethane while maintaining the reaction mixture temperature below 0° C. The reaction mixture is stirred for 45 minutes, treated with a solution of trans-3-dimethylaminoacrylonitrile (16.4 mL, 0.15 mol) in 1,2-dichloroethane, stirred at room temperature for 16 hours, refluxed for two hours and concentrated in vacuo to obtain a semi-solid residue. A solution of the residue in 2-propanol is treated with a solution of oxalic acid dihydrate (18.9 g, 0.15 mol) in 2-propanol and warmed until a clear solution is obtained. The clear solution is cooled to and held at room temperature for several hours, cooled in a freezer for two hours and filtered. The filter cake is washed sequentially with 2-propanol and ether and dried in a vacuum desiccator at 50° to give the title product (28.6 g, 79%).

EXAMPLE 2

Preparation of Methyl 4-cyanopyrrole-2-carboxylate and 4-Cyanopyrrole-2-carboxylic acid

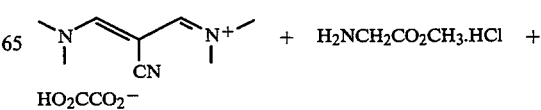

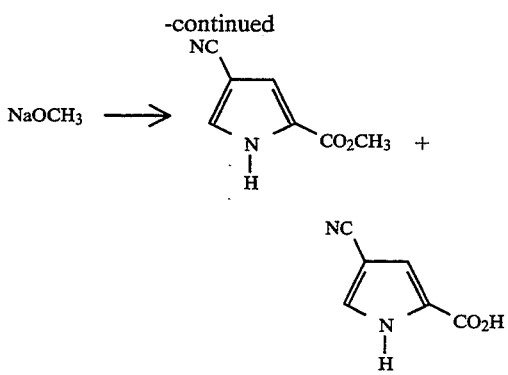

[2-Cyano-3-(dimethylamino)allylidene]-dimethylammonium oxalate (3.6 g, 0.015 mol) is added to a stirred suspension of glycine methyl ester hydrochloride (1.9 g, 0.015 mol) and sodium methoxide (3.2 g, 0.06 mol) in N,N-dimethylformamide which has been cooled in an ice/acetone bath. The reaction mixture is heated to and held at 120° C. for 16 hours, cooled to room temperature and concentrated in vacuo to obtain a semi-solid residue. The residue is partitioned between ethyl acetate and cold, dilute hydrochloric acid. The layers are separated and the aqueous layer is washed with ethyl acetate. The organic layer and washes are combined, washed sequentially with water and brine, dried over anhydrous magnesium sulfate and concentrated in vacuo to give a mixture of the title products as a tan solid (0.85 g). The mixture contains about 70% methyl 4-cyanopyrrole-2-carboxylate and about 30% 4-cyanopyrrole-2-carboxylic acid.

EXAMPLE 3

Preparation of 2,4,5-Tribromopyrrole-3-carbonitrile

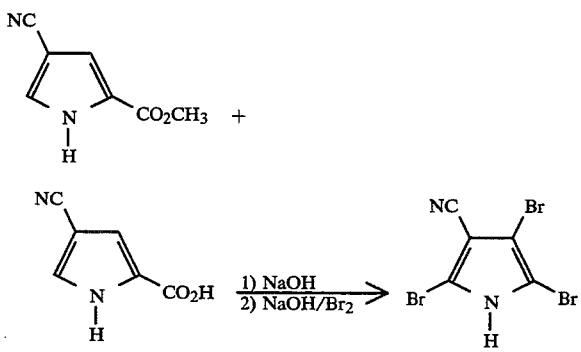

Sodium hydroxide (50% in water, 0.4 mL) is added to a solution of the mixture obtained in Example 2 (0.85 g) in dioxane. The reaction mixture is heated at 80° C. for about 12 hours, cooled to about 10° C. and treated with additional sodium hydroxide (50% in water, 1.2 mL). Bromine (0.9 mL, 0.02 mol) is then added portionwise over 90 minutes to the reaction mixture while maintaining the temperature below 20° C. After the addition is complete, the cooling bath is removed and the reaction mixture is stirred for 90 minutes then poured into water. The aqueous mixture is acidified with hydrochloric acid and filtered. The filter cake is washed with water and dried to give the title product as a tan solid (0.72 g).

I claim:

1. A process for the preparation of 2,4,5-tribromopyrrole-3-carbonitrile which comprises reacting a vinamidinium salt having the structural formula

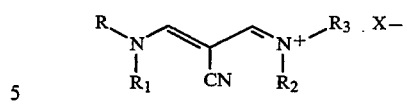

wherein
R, $R_1$, $R_2$ and $R_3$ are each independently $C_1$-$C_4$ alkyl, or when taken together, R and $R_1$, and $R_2$ and $R_3$, may form a 5- or 6-membered ring in which each of $RR_1$ and $R_2R_3$ are represented by the structure —$(CH_2)_4$— or —$(CH_2)_5$—; and
$X^-$ is an anion;
with a glycine ester having the structural formula

wherein $R_4$ is $C_1$-$C_4$ alkyl;
and a first base in the presence of a first solvent to form a mixture comprising 4-cyanopyrrole-2-carboxylic acid and a 4-cyanopyrrole-2-carboxylate having the structural formula

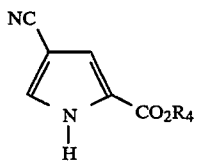

wherein $R_4$ is as described above, hydrolyzing said mixture with a second base in the presence of a second solvent to form a 4-cyanopyrrole-2-carboxylic acid salt, and reacting said 4-cyanopyrrole-2-carboxylic acid salt with a third base and a brominating agent in the presence of a third solvent to form said 2,4,5-tribromopyrrole-3-carbonitrile.

2. The process according to claim 1 wherein the first base is selected from the group consisting of an alkali metal $C_1$-$C_6$ alkoxide and an alkaline earth metal $C_1$-$C_6$ alkoxide; the second base is selected from the group consisting of an alkali metal hydroxide and an alkaline earth metal hydroxide; and the third base is selected from the group consisting of an alkali metal hydroxide and an alkaline earth metal hydroxide.

3. The process according to claim 2 wherein the first base is sodium methoxide, the second base is sodium hydroxide, and the third base is sodium hydroxide.

4. The process according to claim 1 wherein the first solvent is selected from the group consisting of N,N-dimethylformamide and a $C_1$-$C_6$ alcohol; the second solvent is selected from the group consisting of water, and a water-miscible ether or mixtures thereof; and the third solvent is selected from the group consisting of water, and a water-miscible ether or mixtures thereof.

5. The process according to claim 4 wherein the first solvent is N,N-dimethylformamide; the second solvent is selected from the group consisting of water, dioxane, and tetrahydrofuran or mixtures thereof; and the third solvent is selected from the group consisting of water, dioxane, and tetrahydrofuran or mixtures thereof.

6. The process according to claim 1 wherein the brominating agent is selected from the group consisting of bromine, pyridinium bromide perbromide and N-bromosuccinimide.

7. The process according to claim 6 wherein the brominating agent is bromine.

8. The process according to claim 1 wherein R, $R_1$, $R_2$ and $R_3$ are each independently $C_1$–$C_4$ alkyl; and $X^-$ is selected from the group consisting of $BF_4^-$, $ClO_4^-$, $HO_2CCO_2^-$ and $Cl^-$.

9. The process according to claim 8 wherein R, $R_1$, $R_2$, $R_3$ and $R_4$ are each methyl.

10. The process according to claim 1 wherein the glycine ester is present in the amount of about 1 to 5 molar equivalents, the first base is present in the amount of about 2 to 6 molar equivalents, the second base is present in the amount of about 1 to 8 molar equivalents, the third base is present in the amount of about 4 to 8 molar equivalents, and the brominating agent is present in the amount of about 3 to 9 molar equivalents.

11. The process according to claim 1 wherein the vinamidinium salt is reacted with the glycine ester and the first base at a temperature of about 50° C. to 140° C., the mixture is hydrolyzed with the second base at a temperature of about 25° C. to 90° C., and the 4-cyano-pyrrole-2-carboxylic acid salt is reacted with the third base and the brominating agent at a temperature of about 0° C. to 25° C.

* * * * *